US00PP34929P2

(12) United States Plant Patent
Koot

(10) Patent No.: US PP34,929 P2
(45) Date of Patent: Jan. 17, 2023

(54) ***PETUNIA* PLANT NAMED 'DOPETDURAYE'**

(50) Latin Name: ***Petunia* X *hybrida***
Varietal Denomination: Dopetduraye

(71) Applicant: DUMMEN GROUP B.V., De Lier (NL)

(72) Inventor: Arjan Koot, Oeffelt (NL)

(73) Assignee: Dummen Group B.V., De Lier (NL)

( * ) Notice: Subject to any disclaimer, the term of this patent is extended or adjusted under 35 U.S.C. 154(b) by 0 days.

(21) Appl. No.: 17/705,318

(22) Filed: Mar. 26, 2022

(51) Int. Cl.
*A01H 5/02* (2018.01)
*A01H 5/10* (2018.01)
*A01H 6/82* (2018.01)

(52) U.S. Cl.
USPC ..... Plt./356.15
CPC ..... *A01H 5/02* (2013.01); *A01H 5/10* (2013.01); *A01H 6/824* (2018.05)

(58) Field of Classification Search
USPC ..... Plt./356.15
CPC ..... A01H 6/824
See application file for complete search history.

*Primary Examiner* — Anne Marie Grunberg
(74) *Attorney, Agent, or Firm* — C. Anne Whealy

(57) ABSTRACT

A new and distinct cultivar of *Petunia* plant named 'Dopetduraye', characterized by its relatively compact, upright and mounding to hanging plant habit; moderately vigorous growth habit and moderate growth rate; freely branching habit; early and freely flowering habit; large white-colored flowers with yellow green-colored centers and venation; and good garden performance.

2 Drawing Sheets

Figure 1:
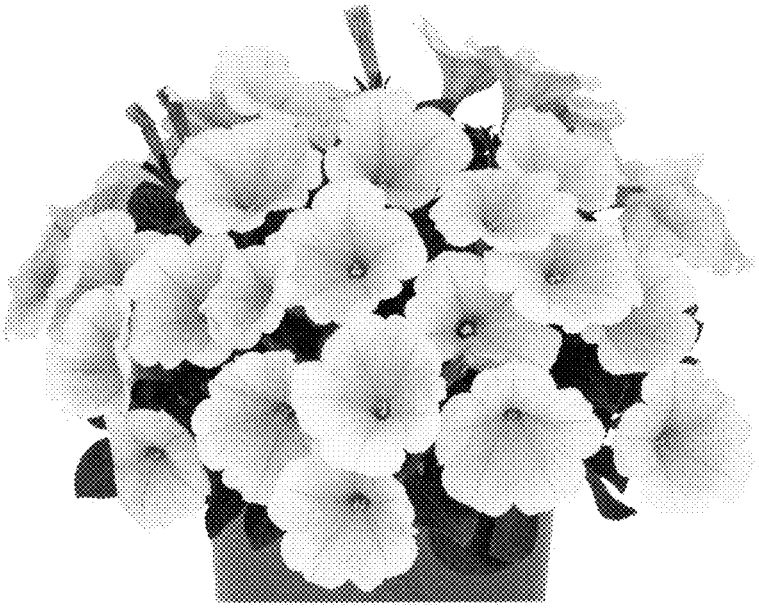

Botanical designation: *Petunia* X *hybrida.*
Cultivar denomination: 'DOPETDURAYE'.

STATEMENT REGARDING PRIOR DISCLOSURES BY INVENTOR/APPLICANT & ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Petunia* plant, botanically known as *Petunia* X *hybrida* and hereinafter referred to by the name 'Dopetduraye'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July, 2018 in Rheinberg, Germany of a proprietary selection of *Petunia* X *hybrida* identified as code number TT17-137139-003, not patented, as the female, or seed, parent with a proprietary selection of *Petunia* X *hybrida* identified as code number TT14-004608-005-X0001, not patented, as the male, or pollen, parent. The new *Petunia* plant was discovered and selected by the Inventor as a single flowering plant from within the progeny of the stated cross-pollination in a controlled greenhouse environment in Rheinberg, Germany in May, 2021.

Asexual reproduction of the new *Petunia* plant by terminal vegetative cuttings in a controlled greenhouse environment in Rheinberg, Germany since June, 2021 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetduraye'. These characteristics in combination distinguish 'Dopetduraye' as a new and distinct *Petunia* plant:

1. Relatively compact, upright and mounding to hanging plant habit.
2. Moderately vigorous growth habit and moderate growth rate.
3. Freely branching habit.
4. Early and freely flowering habit.
5. Large white-colored flowers with yellow green-colored centers and venation.
6. Good garden performance.

Plants of the new *Petunia* can be compared to plants of the female parent selection. In side-by-side comparisons, plants of the new *Petunia* differ primarily from plants of the female parent selection in flower color as flowers of plants of the new *Petunia* are white in color with yellow green-colored centers and venation whereas flowers of plants of the female parent selection are white in color.

Plants of the new *Petunia* can be compared to plants of the male parent selection. In side-by-side comparisons, plants of the new *Petunia* differ primarily from plants of the male parent selection in growth habit as plants of the new *Petunia* are more vigorous than plants of the male parent selection. In addition, plants of the new *Petunia* have larger flowers than plants of the male parent selection.

Plants of the new *Petunia* can be compared to plants of *Petunia* X *hybrida* 'Sunsurf Kitatsu', disclosed in U.S. Plant Pat. No. 25,400. In side-by-side comparisons, plants of the new *Petunia* and 'Sunsurf Kitatsu' differ primarily in the following characteristics:

1. Plants of the new *Petunia* are more compact than plants of 'Sunsurf Kitatsu'.
2. Plants of the new *Petunia* have larger and darker green-colored leaves than plants of 'Sunsurf Kitatsu'.
3. Plants of the new *Petunia* flower about one week earlier than plants of 'Sunsurf Kitatsu'.
4. Plants of the new *Petunia* have larger flowers than plants of 'Sunsurf Kitatsu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a top perspective view of a typical flowering plant of 'Dopetduraye' grown in a container.

Figure 2:
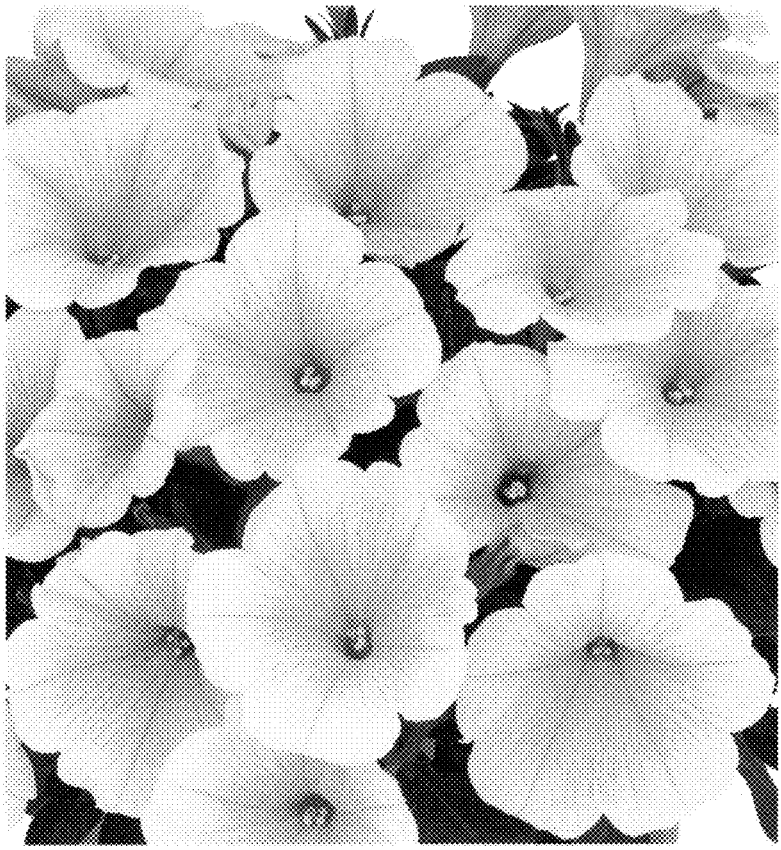

The photograph on the second sheet (FIG. 2) is a close-up view of a typical flowering plant of 'Dopetduraye'.

DETAILED BOTANICAL DESCRIPTION

The aforementioned photographs and following observations, measurements and values describe plants grown during the spring and early summer in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks old when the photographs were taken and 25 weeks old when the description was taken. In the following description, color references are made to The Royal Horticultural Society Colour Chart, Fifth Edition, except where general terms of ordinary dictionary significance are used.

Botanical classification: *Petunia* X *hybrida* 'Dopetduraye'.

Parentage:

*Female, or seed, parent*.—Proprietary selection of *Petunia* X *hybrida* identified as code number TT17-137139-003, not patented.

*Male, or pollen, parent*.—Proprietary selection of *Petunia* X *hybrida* identified as code number TT14-004608-005-X0001, not patented.

Propagation:

*Type*.—By terminal vegetative cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 155B in color, actual color of the roots is dependent on substrate composition, water quality, fertilizers, substrate temperature and age of roots.

*Rooting habit*.—Freely branching; dense.

Plant description:

*Plant and growth habit*.—Relatively compact, upright and mounding to hanging plant habit; freely branching habit with about eight primary lateral branches each with about seven secondary branches developing after pinching; moderately vigorous growth habit and moderate growth rate.

*Plant height, soil level to top of foliar plane*.—About 16.5 cm.

*Plant height, soil level to top of floral plane*.—About 25 cm.

*Plant diameter*.—About 62 cm.

Lateral branch description:

*Length*.—About 30 cm.

*Diameter*.—About 6 mm.

*Internode length*.—About 1.6 cm.

*Strength*.—Moderately strong.

*Aspect*.—Initially upright to somewhat outwardly spreading.

*Texture and luster*.—Pubescent; semi-glossy.

*Color, developing and developed*.—Close to 144A and at the internodes, close to 144C.

Leaf description:

*Arrangement*.—Before flowering, alternate; after flowering, opposite; simple.

*Length*.—About 5.5 cm.

*Width*.—About 3.3 cm.

*Shape*.—Spatulate.

*Apex*.—Obtuse.

*Base*.—Attenuate.

*Margin*.—Entire.

*Texture and luster, upper and lower surfaces*.—Pubescent; leathery; semi-glossy.

*Venation pattern*.—Pinnate; arcuate.

*Color*.—Developing leaves, upper surface: Close to 137B. Developing leaves, lower surface: Close to 137C. Fully expanded leaves, upper surface: Close to 137A; venation, close to 144B. Fully expanded leaves, lower surface: Close to 144A; venation, close to 144B.

*Petioles*.—Length: About 1.1 cm. Diameter: About 3.7 mm. Strength: Moderately strong; firm. Texture and luster, upper and lower surfaces: Smooth, glabrous; matte. Color, upper and lower surfaces: Close to 144B.

Flower description:

*Flower type and flowering habit*.—Single salverform flowers arising from leaf axils; freely flowering habit with usually about 290 flowers and flower buds developing per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about two to three days on the plant; flowers persistent.

*Flower buds*.—Length: About 4.8 cm. Diameter: About 7 mm. Shape: Ovoid. Texture and luster: Rippled; semi-glossy. Color: Close to 144C.

*Flower diameter*.—About 6.7 cm by 7 cm.

*Flower depth* (*height*).—About 6.5 cm.

*Flower throat diameter*.—About 1.2 cm.

*Flower tube length*.—About 3.2 cm.

*Flower tube diameter, proximally*.—About 1.1 cm.

*Corolla*.—Arrangement: Five petals fused at the base and opening into a flared trumpet. Petal lobe length (from throat): About 3.9 cm. Petal lobe width: About 3.4 cm. Petal shape: Roughly spatulate. Petal apex: Obtuse. Petal margin: Entire; slightly undulate. Petal texture and luster, upper and lower surfaces: Rippled, glabrous; semi-glossy. Throat texture and luster: Rippled; semi-glossy. Tube texture and luster: Rippled; semi-glossy. Color: Petal lobe, when opening, upper surface: Close to 150D. Petal lobe, when opening, lower surface: Close to 150B to 150C. Petal lobe, fully opened, upper surface: Close to 155D; venation, close to 151B; color does not change with subsequent development. Petal lobe, fully opened, lower surface: Close to 155D; venation, close to 151C and 149A; color does not change with subsequent development. Flower throat: Close to 151C; venation, close to 151A. Flower tube: Close to 145B; venation, close to 145A.

*Sepals*.—Arrangement: Five sepals fused at the base forming a tubular star-shaped calyx. Length: About 1.2 cm. Diameter: About 2 mm. Shape: Oblong. Apex: Rounded. Base: Decurrent. Margin: Entire. Texture and luster, upper and lower surfaces: Pubescent; semi-glossy. Color: When opening and fully opened, upper surface: Close to 137A. When opening and fully opened, lower surface: Close to 137C.

*Peduncles*.—Length: About 2.8 cm. Diameter: About 1.5 mm. Strength: Moderately strong. Texture and luster: Smooth, glabrous; semi-glossy. Color: Close to 144A.

*Reproductive organs*.—Stamens: Quantity per flower: Five. Filament length: About 2.6 cm. Filament color: Close to 145C. Anther length: About 1.5 mm. Anther shape: Ovate. Anther color: Close to 8C. Pollen amount: Abundant. Pollen color: Close to 11C. Pistils: Quantity per flower: One. Pistil length: About 3.1 cm. Style length: About 2.4 cm. Style color: Close to 145B. Stigma diameter: About 2 mm. Stigma shape: Rounded. Stigma color: Close to 144B. Ovary color: Close to 145A. Fruits: Quantity produced per plant: About 100 during the flowering season. Length: About 4 mm. Diameter: About 2.5 mm. Texture: Smooth, glabrous. Color: Close to 161C. Seeds: Quantity per flower: About 20. Length: About 0.2 mm. Diameter: About 0.2 mm. Texture: Smooth, glabrous. Color: Close to 200A.

Garden performance: Plants of the new *Petunia* have been observed to have good garden performance and tolerate wind, rain, temperatures ranging from about 5° C. to about 40° C. and to be suitable for USDA Hardiness Zone 11.

Pathogen & pest resistance: To date, plants of the new *Petunia* have not been observed to be resistant to pathogens and pests common to *Petunia* plants.

It is claimed:

1. A new and distinct *Petunia* plant named 'Dopetduraye' as illustrated and described.

* * * * *